(12) United States Patent
Delamarche et al.

(10) Patent No.: US 10,345,244 B2
(45) Date of Patent: Jul. 9, 2019

(54) DIAGNOSTIC TEST DEVICE WITH PATTERNED MATERIAL SPOTS

(71) Applicant: International Business Machines Corporation, Armonk, NY (US)

(72) Inventors: Emmanuel Delamarche, Thalwil (CH); Onur Goekce, Zurich (CH); Yuksel Temiz, Lüssiweg (CH)

(73) Assignee: International Business Machines Corporation, Armonk, NY (US)

(*) Notice: Subject to any disclaimer, the term of this patent is extended or adjusted under 35 U.S.C. 154(b) by 165 days.

(21) Appl. No.: 15/173,459

(22) Filed: Jun. 3, 2016

(65) Prior Publication Data

US 2017/0350821 A1    Dec. 7, 2017

(51) Int. Cl.
*G01N 21/84*    (2006.01)
*B01L 3/00*    (2006.01)
(Continued)

(52) U.S. Cl.
CPC ........ *G01N 21/8483* (2013.01); *B01L 3/5023* (2013.01); *B01L 3/54* (2013.01); *G01N 35/00069* (2013.01); *G01N 35/00732* (2013.01); *B01L 2300/021* (2013.01); *B01L 2300/0636* (2013.01); *B01L 2300/0663* (2013.01);
(Continued)

(58) Field of Classification Search
None
See application file for complete search history.

(56) References Cited

U.S. PATENT DOCUMENTS 4,878,588 A * 11/1989 Ephraim .............. A61J 9/02
215/11.2
8,765,062 B2    7/2014 Linder
(Continued)

FOREIGN PATENT DOCUMENTS

WO    WO 2015055738 A    4/2015

OTHER PUBLICATIONS

Myra T Koesdjojo et al, Low-cost, high-speed identification of counterfeit antimalarial drugs on paper. Talanta, Department of Chemistry, Oregon State University, vol. 130, Dec. 1, 2014, pp. 122-127.
(Continued)

*Primary Examiner* — Xiaoyun R Xu
(74) *Attorney, Agent, or Firm* — Daniel P. Morris; Otterstedt, Wallace & Kammer, LLP

(57) ABSTRACT

A test device is configured for diagnostic testing and includes an optical readable medium, in turn including a pattern of spots of material arranged on a surface of the device. Several patterns may be provided. The patterns accordingly formed may be human and/or machine readable. They may notably encode security information, e.g., indicating whether the device has already been used. The spots may notably be inkjet spotted. In addition, a method is provided for decoding information encoded in a pattern of such a test device. In embodiments, liquid is introduced in the device, which comprises additional spots having a substantially different solubility than spots forming the actual pattern. Thus, the additional spots get solubilized in and flushed by the liquid as the latter wets them, and an initially hidden pattern may be read, which is formed of the remaining spots (not solubilized). Encoding methods are also provided.

16 Claims, 5 Drawing Sheets

(51) Int. Cl.
 G01N 35/00 (2006.01)
 *G01N 21/77* (2006.01)
 *G01N 21/78* (2006.01)

(52) U.S. Cl.
 CPC .......... *B01L 2300/0816* (2013.01); *B01L 2300/0864* (2013.01); *B01L 2300/0887* (2013.01); *B01L 2300/126* (2013.01); *B01L 2400/0418* (2013.01); *B01L 2400/0424* (2013.01); *G01N 21/78* (2013.01); *G01N 2021/7793* (2013.01); *G01N 2021/8488* (2013.01); *G01N 2035/00108* (2013.01); *G01N 2035/00772* (2013.01)

(56) References Cited

U.S. PATENT DOCUMENTS

| 2006/0062734 | A1 | 3/2006 | Melker |
| 2012/0122197 | A1* | 5/2012 | Jospeh ............... G01N 27/3272 435/283.1 |

OTHER PUBLICATIONS

Kevin M Schilling et al, Paper and toner three-dimensional fluidic devices: programming fluid flow to improve point-of care diagnostics. Lab on a chip, issue 4, 2013. Abstract only p. 1.

* cited by examiner

DIAGNOSTIC TEST DEVICE WITH PATTERNED MATERIAL SPOTS

BACKGROUND

The invention relates in general to the field of test devices for diagnostic testing, such as rapid testing devices (e.g., point-of-care test devices and over-the-counter tests). In particular, the invention is directed to devices comprising an optical readable medium, formed by a pattern of spots of material, which may for instance encode security features.

Rapid diagnostic test (RDT) devices are devices used for quick and easy medical diagnostic tests. They typically allow results to be obtained within a few hours or less. They notably include point-of-care (POC) test devices and over-the-counter (OTC) tests.

Point-of-care (POC) test devices are known and these devices relate to point-of-care testing, also called bedside testing. Such devices allow medical diagnostic testing at or near the point of care, e.g., at the time and place of the patient care. Over-the-counter (OTC) tests are similar devices. They are, however, typically simpler than POC devices and can often be purchased in pharmacies for people to perform the test themselves, e.g., at home or away from healthcare settings and without assistance from healthcare staff.

Such test devices are typically portable, e.g., handheld devices, easy to use, low cost to manufacture, and fast. They are therefore considered an essential technology by the World Health Organization (WHO) for combatting infectious diseases, amongst others, and improving health in countries where such diseases are endemic. OTC devices are frequently used for monitoring therapy (e.g., to ensure appropriate doses of blood anticoagulant drugs), for monitoring glucose in blood, or for detecting drugs of abuse in body fluids.

The most widely used diagnostic devices are perhaps the so-called "lateral flow assays", which rely on a stripe of cellulose along which a sample flows and reacts with reagents. Such devices are also called strip tests and are typically provided in the form of sticks to be dipped into a liquid to perform the test. If analytes are present in the sample, a colored signal appears on the stripe. Such tests are used to detect malaria, hepatitis virus, HIV, biomarkers related to heart failure, etc.

Besides diseases, test devices as contemplated herein are commonly used to detect a specific condition, such as pregnancy or ovulation.

There has been numerous reports and alerts on such tests being counterfeited or inappropriately sold. For instance, several sources have reported that counterfeited tests had been sold for diagnosing Leishmaniasis. In addition, fake pregnancy tests, fake tests for glucose monitoring and fake human immunodeficiency virus (HIV) test kits (originally designed to test for pregnancy or other conditions) have reportedly been sold, amongst other frauds.

The WHO estimates that counterfeiting of tests compromises the detection, surveillance and eradication of some diseases. This is particularly worrying for large-scale infectious diseases as the latter typically need concerted and global surveillance. The programs of prevention, treatment, detection, and eradication that are developed to combat such diseases sometimes require concerted efforts between several countries. They typically involve heterogeneous types of patients and healthcare settings (e.g., itinerant outpost vs. hospital). A task force called IMPACT (http://apps.who.int/impact/en/) has therefore been setup to provide recommendation and raise awareness on the problem of counterfeiting of medical products. This task force focuses on counterfeited drugs and gives useful recommendations on common approaches for adding security features to medical product packages.

Unfortunately, such security features are frequently breached in practice.

SUMMARY

According to a first aspect, the present invention is embodied as a test device, such as a RDT device. This device is generally configured for diagnostic testing. In addition, it comprises an optical readable medium, wherein the medium comprises a pattern of spots of material arranged on a surface of the device.

Said spots may notably be inkjet spotted, to ensure an accurate placement of the spot and reasonable fabrication times. Several patterns may be present, at distinct locations on the device. The patterns accordingly formed may be human and/or machine readable. They may notably encode security information, e.g., a security key, or be designed to reveal a pattern indicating whether the device has already been used.

Preferably, the test device further comprises a cover covering said pattern of spots, where the cover is transmissive to light. The material spots forming the pattern are thus located under the cover, which make them harder to reproduce or imitate.

In embodiments, the device further comprises a liquid inlet and a flow path, wherein the flow path extends from the liquid inlet. The spots are arranged on said surface, within the flow path. This makes it harder to fake the pattern. All the more, this enables to reveal a hidden pattern, as discussed below.

In typical embodiments, the flow path comprises reagents for enabling said diagnostic testing. In that case, the material spots that form the pattern are preferably located downstream the reagents, with respect to the liquid inlet.

In embodiments, the test device may comprise several flow paths. The device may notably comprise a second flow path extending from said liquid inlet. The reagents and the pattern may accordingly be located in distinct flow paths.

Said surface may notably be a surface of a material impregnated with said reagents, such as a cellulose material. In variants, the device may comprise one or more microchannels, wherein one (or more) of the microchannels comprise(s) a pattern of spots of material such as described above.

Preferably, said spots comprise, each, one or more of: dyes, pigments, liquid metals or alloys, colloids, and proteins. In particular, some of said spots may comprise a temperature-sensitive indicator, for example temperature-sensitive proteins. The above materials may easily be spotted; they furthermore have interesting properties, such as a sufficient optical contrast (for readability) or temperature sensitivity (for tracking inappropriate conditions of storage or transportation). Dyes and/or pigments are preferred, in some applications, for their optical properties and stability, and also for reasons of fabrication costs.

The device may notably comprise a surface material that is one of the following materials: a polymer, silicon dioxide, glass, and cellulose. The surface on which the flow path is formed is a surface of said surface material.

In preferred embodiments, said spots are arranged according to a lattice, e.g., a bi-dimensional lattice. The spots are located at positions corresponding to a subset of cells of this lattice, so as to form said pattern. Each cell of said subset may comprise one or more of said spots of material, to increase the contrast or, more generally, the detectability of the patterns. The lattice may for instance comprise n×m cells, where one or each of n and m is, in general, larger than or equal to 4, for example equal to 16.

In embodiments, said spots are of a first material. The device may further comprise additional spots of a second material, wherein said first material and said second material have a substantially different solubility in a liquid to be used for the diagnostic testing.

Where spots are arranged according to a lattice, the additional spots may be located at positions corresponding to other cells of said lattice, i.e., at locations distinct from those where the first material is spotted, e.g., in a complementary fashion so as to fill in all cells of the lattice and thereby hide a sub-pattern formed by the first material. Because the solubility of the second material may be substantially higher than the first material's, the pattern as obtained after wetting the flow path shall differ from the initial pattern. This, in turns, allows to reveal a sub-pattern (e.g., a message or a key) that is initially hidden in the overall pattern and therefore difficult to fake or tamper with.

In embodiments, the spots are arranged in or on structures formed on said surface according to said lattice, whereby said structures are located at positions corresponding to cells of said lattice. Providing such structures help to better keep the spotted material in position. Said structures may for instance comprise cavities or islets.

Preferably, the average in-plane dimension of the cells is larger than or equal to 100 μm, while two contiguous structures are separated by a gap, which, on average, is larger than, e.g., 10 μm. Thus, the pitch between contiguous cells of said lattice shall typically be larger than or equal to 110 μm, which, in practice, results in very few or even no errors, when spotting droplets in the pixel template, as present Inventors observed.

The average depth of the structures is preferably larger than or equal to 5 μm, to secure the spotted material in the intended cell by capillary pinning of the spotted droplet. Said depth is measured perpendicularly to the average plane of the surface on which the pattern is formed.

According to another aspect, the invention is embodied as a method for decoding information that is encoded in a test device such as described above. This method essentially revolves around optically reading the pattern of spots forming the optical readable medium and decoding information encoded in the pattern read.

In embodiments, this method may further comprise introducing liquid at a liquid inlet of the device, for the liquid to advance along a flow path thereof, where the device comprise additional spots having a substantially different solubility than spots forming the hidden pattern. Thus, the additional spots get solubilized in and flushed by the liquid as the latter wets them. What is next optically read is the (hidden) pattern formed by the remaining spots (not solubilized).

Preferably, decoding comprises, prior to introducing liquid, optically reading one or more initial patterns of spots formed by said spots together with said additional spots.

According to another aspect, the invention is embodied as a method for encoding information in a test device such as discussed above. This method essentially comprises encoding information as a pattern of spots to form an optical readable medium, as described above. The encoding is preferably performed by spotting spots, so as to form the desired pattern of spots.

Devices and methods embodying the present invention will now be described, by way of non-limiting examples, and in reference to the accompanying drawings.

BRIEF DESCRIPTION OF THE DRAWINGS

FIGS. 9-11 are photographs of such patterns, as obtained with islets (FIG. 9), cavities (FIG. 10) or by spotting droplets directly on a cellulose surface (FIG. 11);

FIGS. 12-14 illustrate how a pattern of non-soluble spots can be hidden in a general pattern, thanks to additional, soluble spots. The soluble spots get solubilized and flushed by liquid wetting the flow path in which the pattern is arranged, as in embodiments. FIG. 13 shows a sequence of screenshots captured while operating an actual device, according to embodiments.

Figure 1:
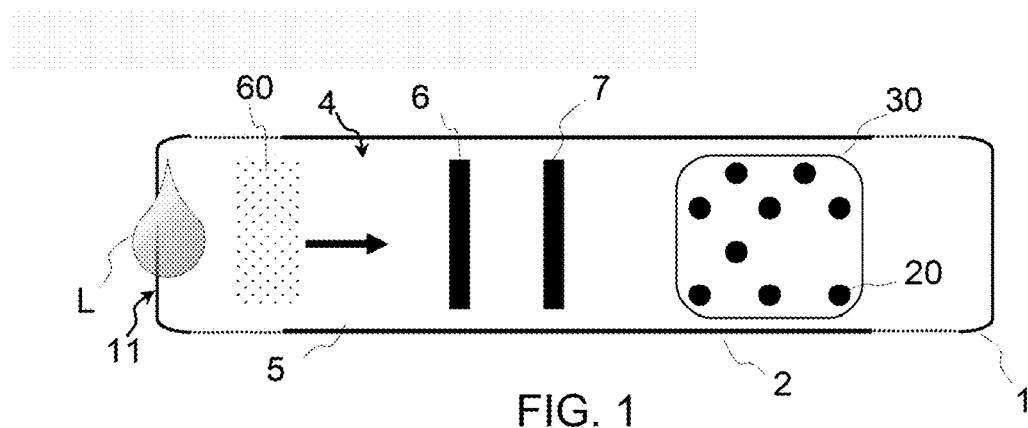
FIG. 1 is a top view of a test device, wherein a pattern of spotted material is arranged within a flow path formed on a surface impregnated with reagents, according to embodiments.

The accompanying drawings show simplified representations of devices or parts thereof, as involved in embodiments. Technical features depicted in the drawings are not necessarily to scale. Similar or functionally similar elements in the figures have been allocated the same numeral references, unless otherwise indicated.

DETAILED DESCRIPTION

As it can be realized, security features can be added directly on test devices (such as strip tests and diagnostic test devices) and not just only on their package. Building on this idea, present inventors developed a novel concept of optical readable media for rapid diagnostic testing.

Referring generally to FIGS. 1-14, an aspect of the invention is first described, which concerns a test device 1-1d. The device is generally configured for diagnostic testing. Diagnostic testing as contemplated here relates to medical diagnostic and, more generally, to determining or analysis of the cause or nature of a problem or situation.

A test device as understood herein may notably be a portable, e.g., handheld device, such as for example a blood glucose meter, a dipstick or a test kit for detecting one or several analytes (e.g., homocysteine, C-reactive protein, glycated hemoglobin or HBA1C, HIV salivary assay, test for cardiac markers, tests for detecting allergens or genetically modified organisms, for the detection of pesticides and pollutants, etc.), or a pregnancy test. More generally, it may be any type of RDT device (POC or OTC device). Furthermore, a test device as understood herein may be used to perform analyses going beyond medical diagnostic, for example for detecting toxins in water, etc. There are potentially numerous applications for such test devices, as the skilled person may realize.

Remarkably, present test devices 1-1*d* comprise an optical readable medium. As illustrated in FIGS. 1-11, this medium is formed by a pattern 30, 32 of spots 20 of material arranged on a surface 4, 5 of the device 1-1*d*.

An optical readable medium may be human- and/or machine-readable medium (also called automated data medium in the latter case). This is a medium encoding data or otherwise exhibiting information in a readable format, e.g., in a format optically readable by an automated device. In the present case, data is encoded via the pattern 30, 32. Several patterns may be provided on a same device, as exemplified in FIGS. 3 and 5, to encode different types of information and/or data, as discussed later in detail.

The material used for the spots 20 has a detectable optical contrast with respect to the surface 4 on which it is formed. This surface need not be plane; it may, on the contrary, be structured, e.g., a channel 10 or, more generally, a flow path 5 may be defined by a wetting surface 4 adjoining a surrounding surface 3, or be structured within a superficial thickness of one or more layer 3 of the device, as known per se. A pattern 30 may be arranged within such a channel or flow path, for reasons that will become apparent later.

A spot 20 of material is a small mark obtained from a material differing in color or texture from the surface 4 around it, similar to a contrasted (or activated) pixel. Such a spot forms a picture element, which, similar to pixels, may denote the smallest controllable elements of a pattern 30, 32. The spots 20 may all be of essentially the same size. Yet, spots 20 of different sizes may be needed, in embodiments, where, e.g., some spots 20 may encode more critical information and accordingly need more contrast, or need be less subject to errors. The size of a spot can for instance be increased by repeatedly spotting droplets at a same location, e.g., within a same cell of a lattice, as exemplified later.

Figure 12:
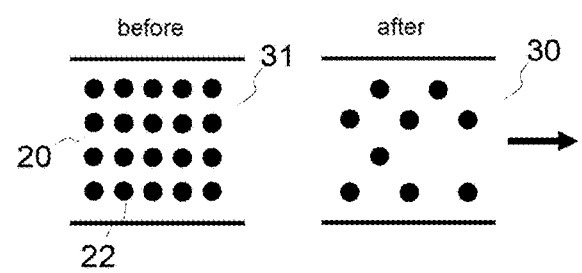
Figure 13:
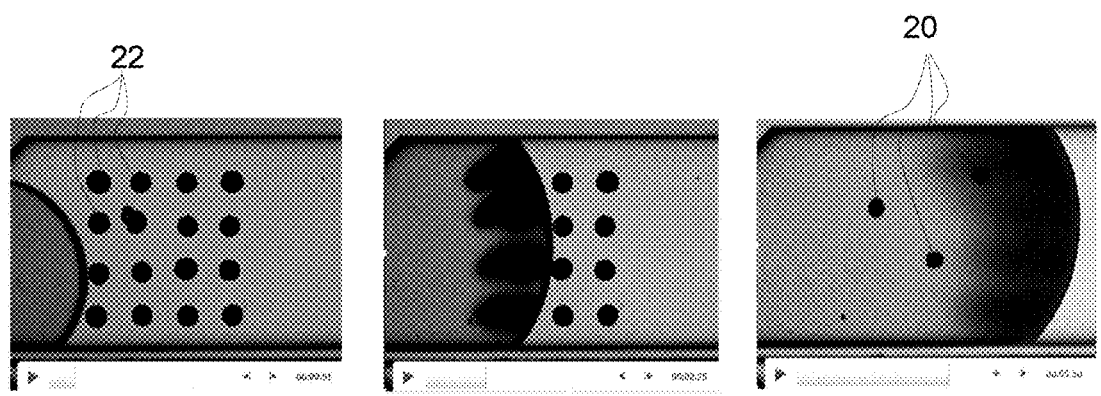
Figure 14:
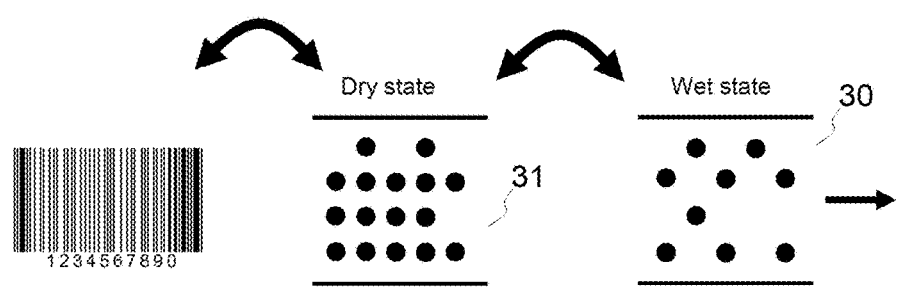

Such spots 20 are typically formed by depositing or spotting liquid drops, e.g., of a colloidal solution containing particles such as colored particles, beads, quantum dots, etc. Said spots can for instance be spotted using an inkjet spotter, or using pin-spotting or quill-spotting. Preferably though, an inkjet spotter is used, to enable easy, accurate and fast spotting. An inkjet spotter can easily handle constantly varying patterns (in mass production). Ink and dyes may for instance be used to form the spots 20, 22. The resulting spots may accordingly have more or less regular shapes, typically round or roundish. Part or all of the spots (see spots 22 in FIGS. 12-14) may be soluble, as discussed below in reference to specific embodiments (FIGS. 12-14).

The actual shapes of the spotted material may also depend on the shape of cells 45 in which they are deposited, if the surface 4 is structured to contain a template of cells 45, e.g., corresponding to a lattice 40 or an array, as discussed below in reference to particular embodiments (FIGS. 6-10).

The patterns 30, 32 of spots 20 allow information to be encoded, for example a security key or any security-related data, fabrication batch id, and/or other human readable information, e.g., as to whether the device was already used or not. The present approach allows information to be encoded directly on the test device 1-1*d*, which is harder to imitate or fake, and may thus be useful to detect fake or counterfeited tests or signalize fraudulent tests, e.g., tests which have already used, as explained below. The patterns 30, 32 may be used in conjunction with other security features on the packaging, e.g., as a confirmation key. The present solutions are perceived to be more satisfactory than solutions relying on security features placed on the sole test packages as the latter can be more easily infringed or faked.

For example, a security key may be spotted directly on the device, to add a technical barrier and discourage counterfeiters. Ideally in such a case, each single test should have an individual security key and the key should be well defined, easy to read and digitalize, e.g., by patterning spots of ink, to obtain an optical pattern.

The following description shows how to define, encode and exploit information such as a security key, patterned directly on a test device. Embodiments discussed herein are more specifically directed to strip tests (lateral flow assays) or toward microfluidics for point-of-care diagnostics.

Referring now more specifically to FIGS. 1-5, present test devices 1-1*d* shall typically comprise a liquid inlet 11, to introduce a liquid L for the test, and a flow path 5 extending from the liquid inlet 11. The flow path is typically defined by one or more wetting surfaces 4, whereon liquid sample can propagate.

Said surface 4 may adjoin a surrounding, non-wetting surface 3, as in FIGS. 2-5. The surface 4 may not be level with the surrounding surface 3 as it is typically deposited, structured, and/or otherwise processed to be wetting. Conversely, the surrounding surface 3 may be processed so as to make a wetting surface non-wetting. The surface 4, or a surface portion forming the flow path, may for instance be structured within a superficial thickness of one or more layers 3 of the device.

In embodiments, the spots 20 forming the patterns 30 are arranged on said surface 4, i.e., within the flow path 5. The liquid inlet 11 need not be explicitly structured on the device, it may for instance simply be, e.g., an end portion of the device 1, e.g., as in the case of a strip test and as assumed in FIG. 1.

Embodiments of the present devices may comprise small bench analyzers. A device 1-1*d* may notably comprise control 6 and signal 7 lines for the assay, as assumed in the depictions of FIGS. 1-5.

If necessary, the present devices may further comprise electrodes arranged in the flow path. As known in, e.g., microfluidics, such electrodes can be connected to an electrical circuit, as appropriate for the test, such as a dielectrophoresis or an electroosmotic circuit. Other electrical circuit components like electrical pads and connections may be patterned on the device or affixed therein, as appropriate and known per se.

Figure 2:
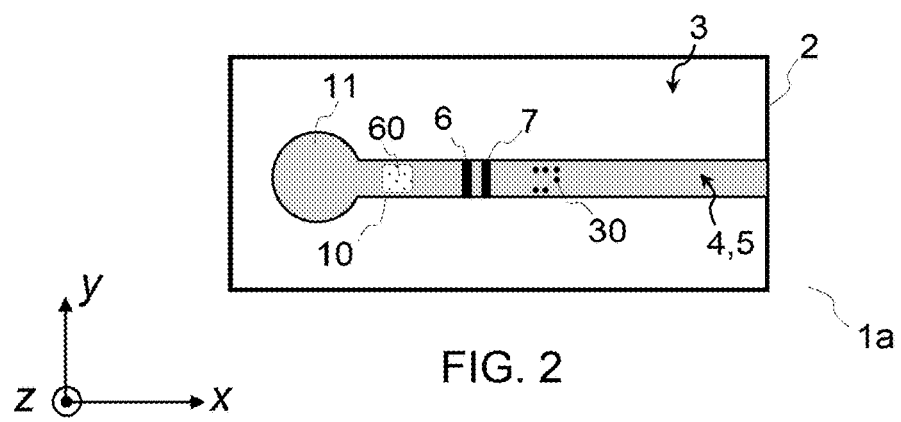
FIGS. 2-4 are top views of a microfluidic, point-of-care test devices, wherein security patterns are spotted within microchannels of the devices, according to other embodiments.
Figure 3:
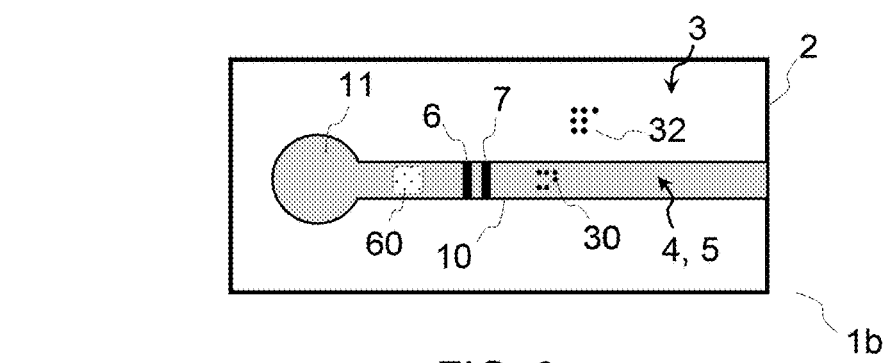

In embodiments, the flow path 5 may comprise reagents 60, for enabling said diagnostic testing, as illustrated in FIGS. 1-3. In such a case, and if a pattern 30 is formed within the flow path 5, then the spots 20 forming this pattern 30 are preferably located downstream the reagents 60 with respect to the liquid inlet 11, to avoid interfering with the test. The pattern 30 may for instance be located downstream the control/signal lines 6, 7.

The test line is typically a line or an area (e.g., rectangle) comprising surface-immobilized receptors, the function of which is to bind a specific analyte in a sample. Such receptors can be for example antibodies, cells, or oligonucleotides. Typically, in addition to being captured by a receptor, the analyte is also bound by another reagent that carries a label capable of generating a signal. Therefore, signal measured on the test line or area reveals the presence of the analyte in the sample and the observed signal is typically proportional to the concentration of the analyte in the sample. The control line is typically a line, or area, comprising an analyte (made by synthesis or obtained by purifying it from natural sources). On this line, or area, of analyte, the reagent carrying the label for generating a signal will bind irrespective of the presence (or not) of analyte in the sample. This serves as positive control. Many tests are performed using this principle, or a similar principle, such as with immunoassays based on lateral flow devices. For example, in some tests, the test line is achieved by coating electrodes with receptors. This corresponds to electrochemical assays such as the well-known strip tests for measuring glucose in blood.

Figure 4:
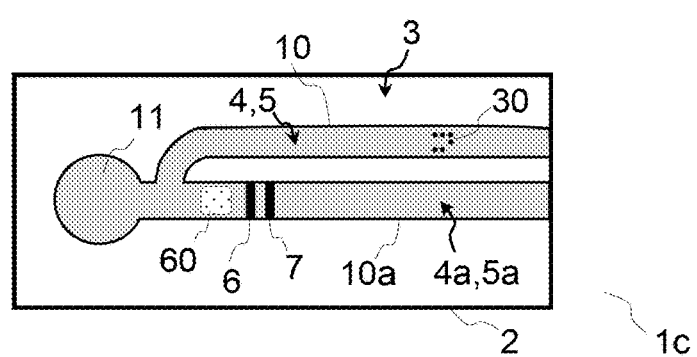

In embodiments, the spots 20 may be patterned within a flow path 5, 10 that is distinct from a primary flow path 5a, 10a that contains the reagents, as in FIG. 4. In that case, the flow path 5 may extend from the primary path 5a or, in variants, directly from the inlet 11. Still, it is noted that not all types of tests involve reagents. For example, some tests may simply be based on the speed of propagation of a liquid, which can be monitored via electrodes extending across the flow path (not shown).

In the embodiment of FIG. 1, the surface 4 forming the flow path 5 is a surface of a material impregnated with reagents 60. Such a material typically comprises a cellulose material, e.g., paper, cardboard, etc., and is otherwise impregnable with liquid, as typically used in test strips or dipstick. The reagents 60 may for instance be spotted using the same technique, e.g., inkjet printing, as used to pattern the spots 20 forming the patterns 30, 32. In variants, reagent may be deposited using any known technique, as appropriate for the test device and the diagnostic testing.

Figure 5:
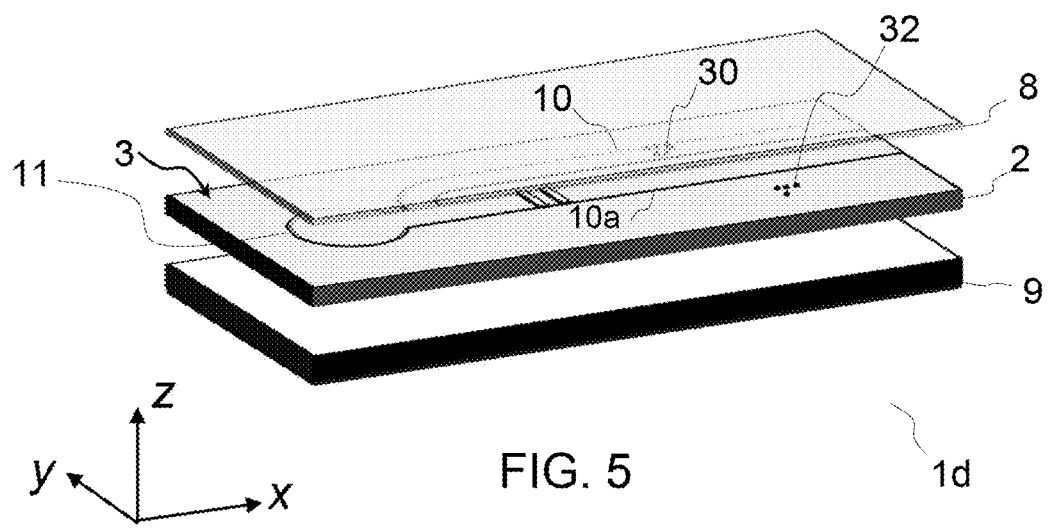
FIG. 5 is a 3D view of a device similar to that of FIG. 4, wherein an additional pattern is arranged outside a microchannel, on a surface of the device, according to embodiments.

Referring now to FIGS. 4, 5, several flow paths 5, 5a may be defined by respective surface portions 4, 4a of the device 1c, 1d, as evoked earlier. One, or each of said flow paths may extend from the liquid inlet 11. Spots 20 can for instance be patterned within a first flow path 5, while the second flow path 5a may comprise reagents 60 for enabling the diagnostic testing. The distinct flow paths 5, 5a are not necessarily formed on a same side of the device. However, they are preferably formed on a same side, be it for the ease of fabrication process or the utilization of the device. Providing distinct flow paths lowers the risk of interference with reagents and sample and may furthermore be leveraged to improve timing control. I.e., based on the expected propagation speed of the liquid, a suitable path length can be calculated for the flow path 5. The pattern 30 is placed in the path 5, at such a distance from the inlet 11 that liquid sample can be expected to reach the pattern 30 at a predetermined time after its introduction via the inlet 11. One may accordingly make sure that the liquid will not reach the pattern 30 until a typical time for the test to complete has elapsed.

Different types of patterns 30, 32 may be relied on. As illustrated in FIGS. 3 and 5, for example, a first pattern 30, which preferably contains both insoluble 20 and soluble spots 22, is formed within the flow path 5, whereas a second pattern 32 (preferably made of insoluble spots, e.g., temperature sensitive) is formed on a surrounding surface 3. When the liquid sample reaches the pattern 30, soluble spots 22 will dissolve so as to reveal a hidden pattern formed by spots 20, as discussed later in detail.

In the embodiments of FIGS. 2-5, the flow paths 5, 5a are formed by channels, e.g., microchannels, as used in microfluidics. The devices 1a-1d can thus be regarded as microfluidic devices. Microfluidic devices are perceived as very promising for point-of-care testing by the present inventors, because such devices can provide very fast tests, are portable, very accurate, and can be multiplexed for detecting several diseases in parallel. Patterning spots 20, 30 on a microfluidic device may require additional care, as later discussed in detail.

The devices 1a-1d depicted in FIGS. 2-5 exhibit one or more microchannels 10, 10a. A pattern 30 is formed within one 10 of the microchannels. A given channel 10a may extend from the liquid inlet 11, which channel 10a enables the primary test, while one or more other channels 10 may extend from the first channel 10a or directly from the same inlet 11. The pattern 30 may be formed in any of such channels 10. Several patterns 30 may be present (not shown), in one or more channels 10, 10a, if necessary. In addition, patterns 32 may be provided outside the channels.

More sophisticated systems of channel junctions may be contemplated. In all case, the dimensions, shapes and/or the flow resistivity of the channels 10, 10a may be designed so as to determine the timing at which the liquid tested will reach the pattern 30. Depending on security method chosen, the timing may matter. For example, one may want liquid sample to reach the pattern 30 only once the test has completed, as said earlier.

One or more additional patterns 32 may be formed outside the channel, as illustrated in FIGS. 3 and 5. An additional pattern 32 may for instance be temperature sensitive, to detect poor logistics, or encode information as to the fabrication batch id of the device, whereas a pattern 30 within a flow path may comprise a liquid sensitive code, which will only be divulged once wetted by the liquid. This is discussed later in detail, in reference to FIGS. 12-14.

Referring more specifically to FIG. 5, in embodiments, present test devices 1d further comprises a cover 8, or a lid, covering the patterns 30, 32 of spots 20. The cover is transmissive to light, to not impair optical detection. The term "cover" is to be understood broadly, it may be any lid or layer capping the device and flow paths thereof, as depicted in FIG. 5. The material spots 20 forming the patterns 30, 32 are thus located under the cover, which makes it harder to imitate, owing to the raised technical barrier.

A cover is especially desirable for microfluidic devices 1a-1d as depicted in FIGS. 2-5, where the lid may fulfil several functions. The lid can indeed be used to close the microchannels and protect the patterns 30, 32. The thickness of the spots forming such patterns is typically small enough to not hinder the sealing by the cover 8. However, and if necessary, the spots forming the additional patterns 32 may be provided in a hollow. Dipsticks need typically not be covered, although the impregnable material that forms the flow path may be partly covered and protected by an outer shell. In the embodiment of FIG. 5, the substrate 2 in which the channels 10, 10a are formed is further typically mounted on a support 9, which confers mechanical stability to the device 1d.

The spots 20 of material may generally comprise one or more of the following: dyes, pigments, liquid metals or alloys, colloids, proteins, beads, colored polymers, gels, oligonucleotides, or compositions thereof. Preferably though, one uses dyes, pigments, liquid metals or alloys, colloids, and proteins, for the reasons explained below. In particular, a temperature-sensitive indicator (comprising, e.g., temperature-sensitive proteins) may be contemplated. Dyes and/or pigments are typically preferred for low-cost devices, owing to their optical properties (e.g., in terms of colors and contrast), stability, and simplicity of fabrication.

Metals can be deposited from a solution precursor, as for example in inkjet printing of silver particles contained in an ink. After drying and sintering, the particles come into contact and form a conductive, planar aggregate. As another example, Gallium, e.g., initially provided as colloids in a liquid phase or as a liquid metal and alloys of gallium can for instance be used. Gallium-based liquid metal alloys are liquid at room temperature and can be inkjet printed. Gallium is not soluble in water and does not react under ambient conditions with air or water. Gallium has a high surface tension (~720 dynes/cm, i.e., approximately 10 times the surface tension of water) and therefore will remain as a droplet while being spotted.

In general, one may want to use low temperature melting metals or alloys, which are liquid (melted) for the purpose of spotting but are solid at room temperature, or in the typical conditions of utilization of the test. In variants, metals (or alloys) may initially be provided as colloids in a liquid phase.

More generally, one may use colloids that comprise beads, nanoparticles, metals, quantum dots, etc. Colloids are solutions with particles having sizes typically between 1 nm and 1000 nm that remain stable and separated in solution. Colloids are particularly appropriate as ink for inkjet printing the material 20, 30 forming the optical readable medium.

Polymers and gels can be functionalized with dyes or fluorescent molecules and can be inkjet spotted using aqueous or organic solvents, depending on their solubility. For example, monomers may be inkjet printed and subsequently crosslinked on the test device, e.g. by UV irradiation.

Proteins can be intrinsically fluorescent, such as green fluorescent proteins or R phycoerythrin. Such proteins have excellent fluorescence properties and can moreover be damaged by excessive heat (R phycoerythrin starts decomposing at 60 C). Such properties can be exploited for monitoring inappropriate storing/handling of test devices in logistics, because of the degradation of the optical pattern they will induce. Patterns 32 formed using such proteins would therefore typically be formed on a surface 3 of the device, outside the flow paths.

Temperature-erasable spots of R phycoerythrin may be exploited to detect an inappropriate logistic. In sophisticated embodiments, the spots forming the patterns 32 may notably comprise pigments that are temperature resistant, in addition to spots of temperature sensitive proteins, which complement the pattern 32. In this case, a poor logistic occurring at any time after manufacturing and before using the test device might be detected due to a degradation of the protein spots and change the pattern 32, so as to reveal a pattern that initially was hidden therein.

Oligonucleotides can be synthetic DNA strands labeled with fluorescent molecules. For some test devices made for example using silicon wafers, the spotted material should be chosen to have sufficient optical contrast. To that aim, beads, pigments, and metals (or alloys) may be preferred. Proteins may also include enzymes and more specifically enzymes that can catalyze the conversion of a soluble reactant into a colored non-soluble product. This reactant can be contained in an area of the test device upstream of the pattern 30 or can be added to a sample. Such enzymatic color producing reactions are commonly used for staining tissue sections and biological specimens.

For completeness, the surface 4 on which the flow path 5 is formed is the surface of a material that shall typically be one of the following materials: a polymer (e.g., a SU-8 polymer), silicon dioxide, glass, and cellulose-based material (paperboard, paper, etc.). Other materials may be contemplated, such as, e.g., a metal coating. However, a metal coating may require a more complex fabrication method (for instance a cleanroom or a complex process), or need toxic precursors.

Referring now to FIGS. 8-14, the spots 20, 22 forming the patterns 30, 31, 32 may, in embodiments, be arranged according to a lattice 40. Different types of lattices may be used in respect of different types of patterns 30, 32, depending on the information to encode or the functions of such patterns, which may be partly, or totally erasable, or not erasable at all.

As notably illustrated in FIGS. 8-11, the lattice may for instance be a bi-dimensional lattice 40. The spots are located at positions that correspond to a subset of cells 45 of the lattice 40, so as to form a pattern 30, 32. The lattice 40 is a systematic arrangement of cells 45, most practically in rows and columns. Each cell of a given lattice preferably has the same dimensions, in which case the steps a, b of the lattice 40, along directions x and y are constant, as assumed in FIG. 8. This eases the design, the fabrication and the deposition processes. In embodiments, the steps a and b are equal, as assumed in FIGS. 12-14.

The cells may be filled by spotting one or more drops therein, to increase the size of the spot and the contrast, if needed. The fabrication process is nevertheless accelerated if only one drop can be spotted per cell, whence the advantage of optimizing the cell size vs. the drop size, as discussed later.

Yet, grids of varying cells 45 may be contemplated, e.g., where some cells 45 need be larger than others, because they will be used to encode more critical information and thus may need more optical contrast, or are less tolerant to errors in the spotting process. The lattice 40 may thus have a non-constant step, in each direction x and y. Accordingly, "lattice" is to be interpreted broadly here, it may be any kind of grid, mesh, or tessellation, having constant steps, or not, and whose cells are addressable, so as to automate the deposition process.

In variants, a one-dimensional lattice may be used. The encoded information is, however, poorer and easier to fake.

The lattice 40 and the resulting patterns 30, 32 may have an aspect ratio, as seen in FIGS. 8-11, where the dimension of the lattice along x is substantially larger than along y. I.e., the largest dimension is parallel to a longitudinal direction of extension of the flow path 5. This, in turn, allows to optimize the density of encodable information, which is especially advantageous where the flow path 5 is provided in a microchannel, owing to typical dimensions and form factor of the latter.

Figure 11:
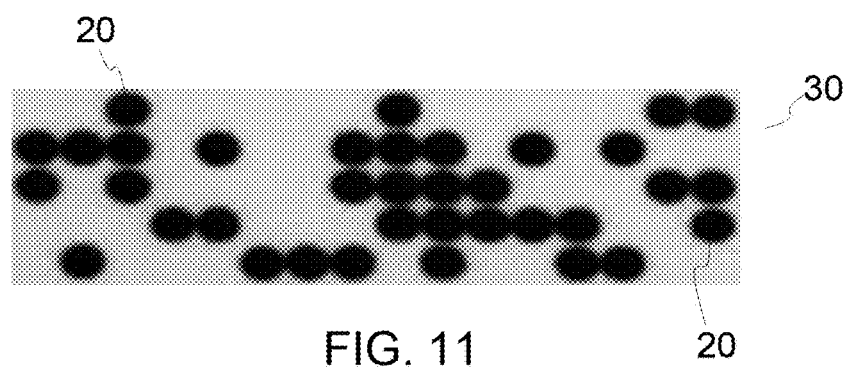

The lattice 40 per se need not be physically structured on the surface 4 of the device 1-1d that forms the flow path 5, for example when a pattern 30 is spotted on cellulose or any other impregnable material, as in FIG. 1 or 11. Still, the pattern 30 may be formed according to an abstract lattice 40 and the spots formed at positions corresponding to cells of this abstract lattice.

However, when the flow path 5 is formed on a surface 4 such as a polymer, $SiO_2$, glass, etc., then the cells 45 of the array may be physically structured within a superficial thickness of the surface 4, to ease the spotting.

Referring now to FIGS. 12-14, in embodiments, the test devices 1-1d may involve spots 20, 22 formed out of different materials, to make it possible to reveal a hidden pattern, as evoked earlier. The materials at stake may notably have a substantially different solubility in the liquid used to perform the diagnostic testing. Thus, first spots 20 may be located at positions corresponding to a subset of the cells 45 (the hidden pattern), whereas additional spots 22 may be located at positions corresponding to complementary cells of the lattice 40, i.e., cells that are distinct from said subset of cells 45 and constitute a second, distinct subset. The juxtaposition of the first and second subsets shall typically map the entire lattice, to form an initial pattern 31 hiding the pattern 30, as illustrated in FIG. 12. This make it possible for a pattern 30 (consisting only of insoluble spots 20) to appear only after the soluble spots 22 were flushed by the liquid as the latter advances in the flow path 5, as otherwise demonstrated in the screen shots of FIG. 13, with a prototype device.

In embodiments, the pitch between contiguous cells 45 of the lattice 40 is larger than or equal to 110 µm. Above this threshold, errors tend to substantially decreases, as further explained below.

The lattice 40 may typically comprises n×m cells 45, where each of n and m is, in general, larger than or equal to 4. For example, a 5×4 lattice may be used, as in FIG. 12. Larger lattices are, however, preferred, such as 16×5, as in FIGS. 8-11. Preferably, the lattice exhibits an aspect ratio, such that n (along x) is larger than m (along y), for the reasons mentioned earlier. In general, a 16×m lattice may advantageously be used when inkjet spotting the patterns 30, 32, so as to exploit the latest generation of inkjet spotters, which may comprise a line of up to 16 nozzles in one row.

Using a grid 40 allows to indicate a user that a code, a key, or any indication was added to a device. Even simple codes may create a technical barrier sufficient to repel fraud. Another level of information may relate to a fabrication batch id. It is indeed typical for diagnostic tests from different batches to exhibit slightly different performances (e.g. sensitivity, error bars, etc.). Calibration tables for specific batches can be used for normalizing test results and the batch can be identified based on the optical code. Codes can benefit from a relatively large number of cells (e.g., 16×m), as necessary, in particular if a unique id need be affixed to each single diagnostic test. E.g., a 16×16 grids with 100×100 µm cells allows encoding ~100 bits/mm$^2$. Yet, 256 bits may be unnecessary, if only a few octets need be encoded. There is a trade-off between the information one wishes to encode (and so the desired level of security) and the affordable fabrication time per device. In variants where simple optical codes are needed, only one row may suffice.

Referring back to FIGS. 6, 7, the lattice 40 may, in embodiments, be physically imprinted on the test devices 1a-1d. That is, structures 41, 43 may be formed on a surface of the device, e.g., on the surface 4 forming the flow path, according to the lattice 40. Said structures 41, 43 are accordingly located at positions corresponding to cells 45 of the lattice 40. The spots 20, 22 are, in turn, arranged in or on such structures 41, 43.

The structures 41, 43 can notably be embodied as cavities or wells (FIGS. 6 and 10), or islets (FIGS. 7 and 9), which relatively simple to fabricate. More generally yet, other types of structures can be contemplated, e.g., that include slanted walls. The lattice preferably comprises only structures of one type (e.g., cavities 41 or islets 43), which preferably have all the same dimensions, to ease the design, the fabrication and the deposition processes.

Figure 6:
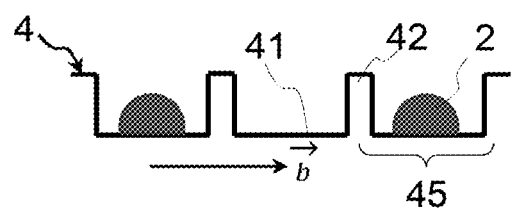
FIGS. 6 and 7 show, each, a 2D cross-sectional view of structures (cavities or wells, FIG. 6, or islets, FIG. 7), used to spot droplets of materials to form a pattern, as involved in embodiments.
Figure 7:
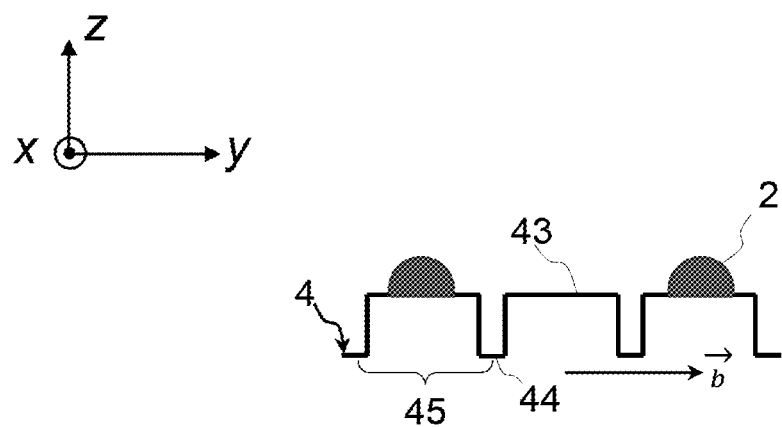
Figure 8:
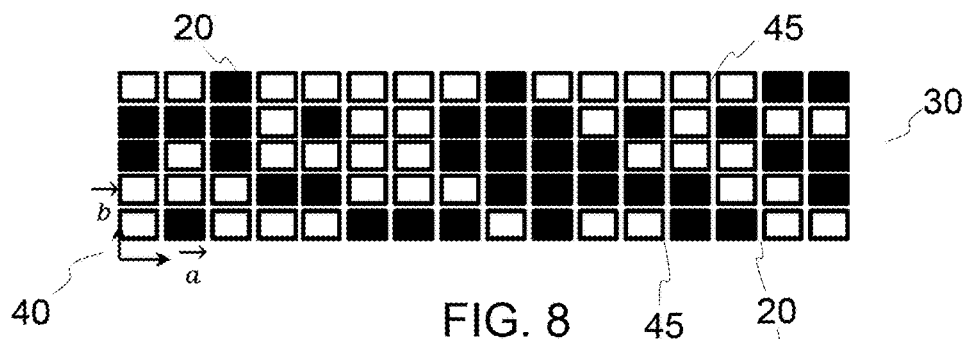
FIGS. 8-14 show examples of bi-dimensional lattices of cells, according to which patterns may be formed, as involved in embodiments. In particular.
Figure 9:
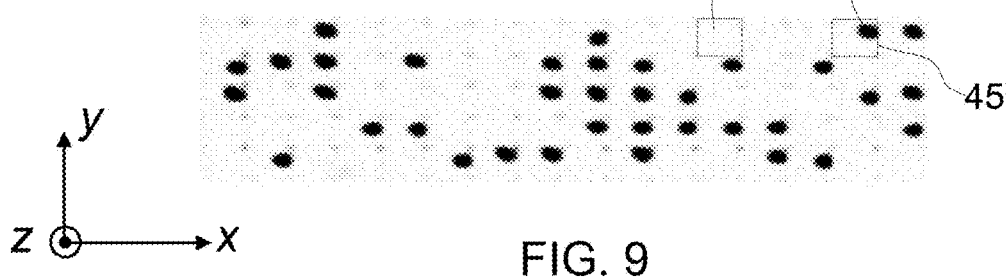
Figure 10:
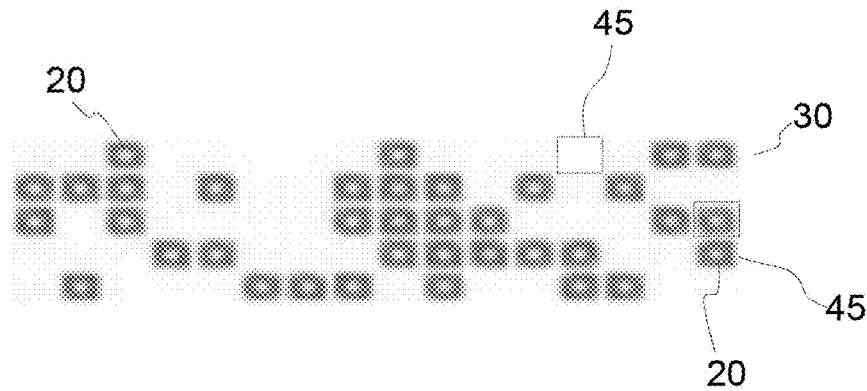

As seen in FIGS. 6 and 7, two contiguous structures 41, 43 are preferably separated by a gap 42, 44. The gaps may most simply consists of raised portions (or walls) 42, to delimit cavities, or of blind holes (or grooves), to delimit islets. Such gaps are preferably larger than 10 µm on average. The gaps are measured in-plane, along a relevant direction between two contiguous cells, i.e., the direction y in the cross-sections of FIGS. 6-7. A minimal gap of 10 µm eases the optical reading and avoids fabrication issues, notably if there is a slight misalignment between the spotter and the ideal cells' positions. The gaps 42, 44 ensure distinctness between the spotted pixels and avoid errors in the deposited spots 20. The capillary effects caused by the gaps (involving corners and the like, see FIGS. 5, 6) prevents liquid drops 20 from wetting other cells and merging.

Preferably the gaps are larger than 25 or even 50 Optimal dimensions generally depend on the inner dimensions of the structures 41, 43, the nature of the liquid sample and the number of drops of the liquid spotted per cell, etc. In embodiments, the gap may reach 75 it being noted that the maximal size of droplets is typically of about 70 µm. A gap larger than 25 or 50 µm ensures a good readability, even when using a low-cost optical detection system. Since a droplet has a size that typically is around 70 µm or less when being ejected by an inkjet nozzle, a larger gap (e.g., of 75 µm) makes sure that a drop does not bridge two adjacent islets.

Typically, spotting is performed using a surface-head distance of ~0.25 mm. A fraction of the droplet may evaporate before the droplet reaches the surface (e.g., up to 20%, depending on ambient relative humidity). Spotting from distances larger than 1 mm strongly increases the risk of evaporation of the droplet and may pose problems when droplets are ejected slightly obliquely from the head. To mitigate this problem, larger gaps (e.g., of 75 µm) can be contemplated. If a spotter needs to be placed further away from the surface due to the presence of topography on the surface, then even larger gaps (≥75 µm) can be contemplated but this will typically require a larger footprint for the pattern 30, 32 on the device and may also affect the cost of the device. If, on the contrary, the head of an inkjet spotter comes too close to the surface of the device, the droplet will land to the surface with its maximum size, such that a 75 µm gap 42, 44 will suffice to avoid placement errors.

In embodiments, the average depth of the structures 41, 43 is larger than or equal to 5 µm. The average depth is measured perpendicularly to the average plane of the surface 4. A depth of 5 µm is sufficient, in practice, to provide satisfactory pinning of the spotted material. Larger depths can nevertheless be contemplated. Yet, the structures 41, 43 should preferably be designed so as for the optical code 30 to be as much as possible co-planar with the test signals. In this manner, both the test result and the optical code 30 can be optically read using the same focal plane. The average depth of the structures 41, 43 shall therefore be smaller than 50 µm, in general.

The average in-plane dimension of the structures 41, 43 is preferably larger than or equal to 100 µm, and more preferably smaller than 500 µm. The average in-plane dimension of the structures is measured parallel to the average plane of the surface 4. The average in-plane dimensions of the structures correspond, e.g., to the average side of a rectangle or a square or to the diameter of a circle, depending on the shape chosen for the structures 41, 43.

Reminding that gaps between such structures 41, 43 are preferably larger than 10 µm, the step or pitch of the lattice 40 will therefore typically be larger than 110 µm. Ensuring such a minimal step results in that very few or no errors subsist, when spotting liquid in the pixel template to form spots 20, as the Inventors observed. This can tentatively be explained by the fact that 50-70 µm drops can still easily be created and precisely spotted, whereas creating and spotting smaller drops is more difficult, owing to competition by the surface 4 tension of the liquid.

A large variety of spotting materials, deposition surface and cell structures, of various dimensions have been tested. When using impregnable materials (without any cells structured thereon), nicely contrasted spots can be obtained, as reflected in FIG. 11. When using cells structured as islets, best results were obtained with 100 µm-wide islets separated by gaps (hollows) of 10 µm (as in FIG. 9). Larger gaps are more visible and may hinder the pattern recognition; they furthermore impact the density and thus the footprint of the optically readable medium. When using cells structured as wells or cavities, best results were obtained with 100 µm-wide wells (cavities) separated by gaps of 10 to 25 µm. Small gaps (e.g., 10 µm, as assumed in FIG. 10) already yield satisfactory results. Larger gaps lead to good results too, but impact the density and thus the footprint. In general, the same cell's and gap's dimensions can be used for both the well and islet structures. All in all, wells are preferred over islets as they lead to better optical properties.

Figure 15:
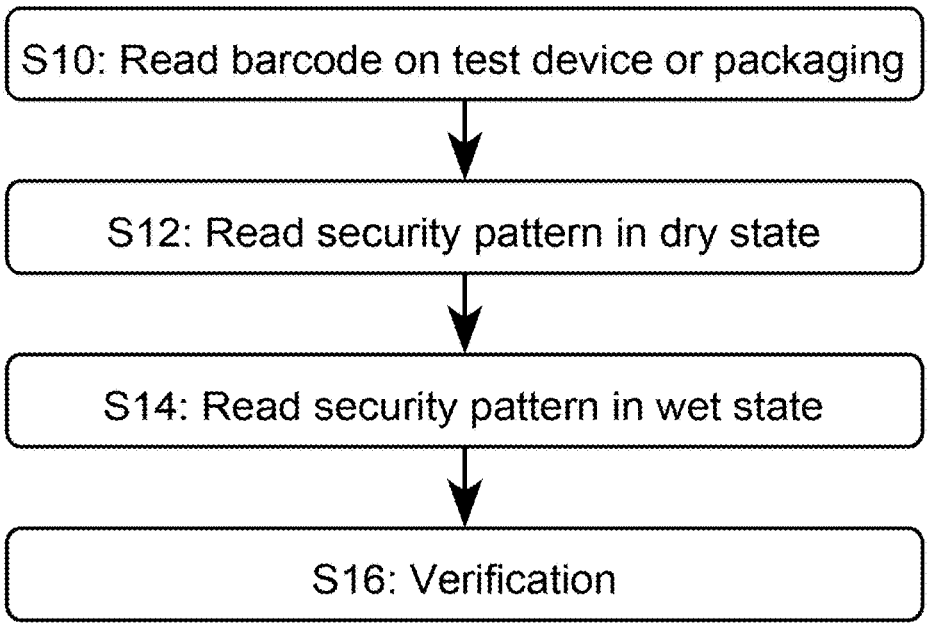
FIGS. 15 and 16 show flowcharts illustrating high-level steps of a method for decoding information encoded in a pattern and a method for encoding such information, respectively, according to embodiments.

So far, the discussion focused on devices. Yet, according to another aspect, the invention can be embodied as a method for decoding information that is encoded in a device 1-1$d$ as described above. Essential aspects of such a method have already been evoked. Such a method is briefly discussed now, in reference to FIG. 15.

Essentially, this method comprises optically reading S12, S14 a pattern 30 of spots 20 forming the optical readable medium, as encoded directly on the test device. Steps S12, S14 may for instance be performed using a handheld device, e.g., a smartphone or a tablet, equipped with a generic or dedicated application, taking control of the camera embedded in the handheld device. In variants, a USB camera, or a specialized or customized optical device may be used to that aim.

Next, information encoded in the pattern 30 read may be decoded S16, using any suitable algorithm, implemented in-situ (e.g., directly at the handheld device), or remotely (the data read is sent to a server for verification).

In variants, steps S12, S14 may be performed thanks to an optical sensor such as a photodiode array mounted on a disposable chip. The latter need not necessarily be part of the same (local or remote) device used to decode the pattern.

Decoding S16 may take place before and/or after use of the test device 1-1$d$. In particular, several patterns 30, 32 may need be optically read and decoded. In preferred embodiments, a pattern 31 is first optically captured while still being in a dry state (see also FIGS. 12 and 14), and subsequently read again in the wet state, where the initial pattern 31 has given way to a new pattern 30. To that aim, soluble spots 22 are used which form part of the pattern 31, as already discussed in reference to FIGS. 12-14. Both patterns 31, 30 may then be involved in a verification process S16. If necessary, a barcode on the packaging of the test device may additionally be read S10, to strengthen security, see FIG. 14.

Several methods are known which allow a digital image to be interpreted from a picture taken. Such techniques have for instance been massively developed for mobile applications, e.g., for interpreting 2D barcodes. If necessary, optical character recognition (OCR) may be involved.

Figure 16:
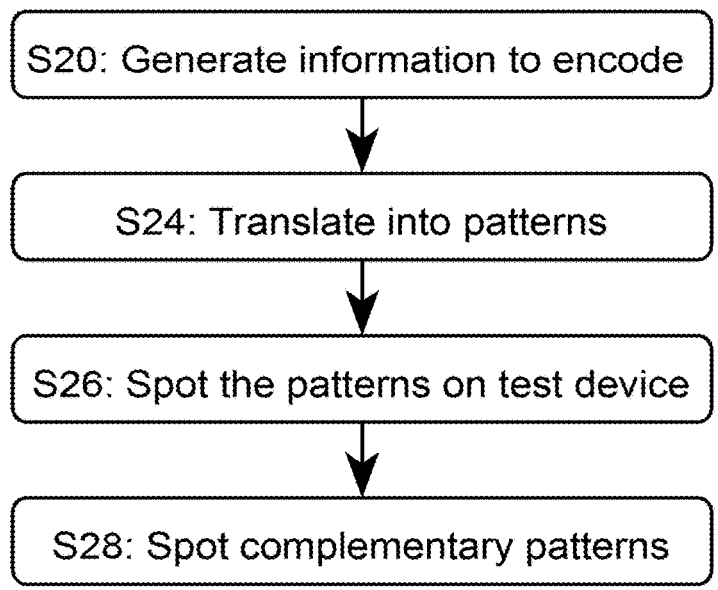

According to a final aspect, the invention can also be embodied as a method for encoding information in a test device, i.e., to obtain a test device 1-1$d$ as described earlier. Such a method is now briefly discussed in reference to FIG. 16.

Essentially, such a method comprises encoding information as a pattern 30, 31 or 32, comprising spots 20, 22, so as to form an optical readable medium. The patterns 30-32 are directly formed on the devices, e.g., by spotting S26-S28 elements 20, 22 to form said patterns. The information needed is generated S20 and translated S24 during a prior phase, thanks to techniques generally known in the art and according to methods that are orthogonal to the present invention.

Where elements 20, 22 have different chemical compositions (e.g., soluble and insoluble elements forming complementary patterns), these are typically deposited at distinct deposition steps S26, S28. Said elements can for instance be spotted using an inkjet spotter, or using pin-spotting or quill-spotting, as known per se.

The above embodiments have been succinctly described in reference to the accompanying drawings and may accommodate a number of variants. Several combinations of the above features may be contemplated. Examples are discussed below.

Embodiments have been heavily tested, experimentally, wherein a pattern 30 comprises a security key 30, which is patterned directly on the diagnostic test device. The key can be complementary to a key on an individual test package or test lot. The key is placed in the vicinity of the test signal area (within the flow path), and comprises insoluble elements, such that it can be read at the same time as the test result. That the key is placed after or adjacent to the test signal areas lowers the risk of interferences between chemicals forming the key and the (bio)chemicals for the test.

Several combinations of key element dimensions, spacing, chemical type, solvent, surface modification, etc., can be contemplated, which enable the key to be geometrically well defined and not spreading or contaminating the test. This matters inasmuch as diagnostic tests are typically wettable and capillary active, so that adding chemicals can easily compromise the test due to contamination, spreading, incompatibility of biochemicals with solvents from the key, etc. However, the key may be based on the same reagents as used for the test, and can therefore be formed during the same fabrication step at which such reagents are deposited.

The key fits in 400 µm-wide channels (whose widths will, in general, be less than 1 mm), structured in a SU-8 3010 surface or a SU-8 3050 surface. The size of the spots is sufficiently small to afford enough key elements. Only few droplets are needed per elements, which result in good optical contrast, with few defects, and so in a well visible key when imaged with a smartphone equipped with an external, low cost macro lens.

The present devices 1$a$-1$d$ may be fabricated as microfluidic devices, as noted earlier. Yet, adding security features on a microfluidic device may be challenging. In particular, we note the following:

- Microfluidics have small microchannels and structures. The pattern elements 20, 22 should be small enough when integrated in microfluidic structures, so as to enable sufficient complexity for the patterns;
- Microchannels and microfluidic structures should not be overflown and flushed with liquids/chemicals used to form the pattern elements 20, 22;
- Adding pattern elements 20, 22 to microfluidic devices that have capillary active areas might spread chemicals from the pattern elements 20, 22 and contaminate surfaces and reagents in the microfluidic chip; and
- The patterning of elements 20, 22 should not adversely affect the filling of structures (for example by pinning a liquid filling front or by having uneven filling where bubbles might be trapped).

In addition, any test device should preferably be designed so as for patterns 30, 32 to be easy to read (i.e., preferably without a microscope or a lens) and have a long shelf lifetime. Finally, the presence of a pattern should be easy to check before starting a test.

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated. For example, other materials and dimensions than those explicitly evoked may be contemplated, in specific applications.

What is claimed is:

1. A test device configured for diagnostic testing, the device comprising:
    a liquid inlet;
    a flow path extending from said liquid inlet;
    an optical readable medium, the medium comprising a pattern of spots of material arranged on a surface of the device within the flow path, wherein the spots are arranged according to a bi-dimensional lattice and are located at positions corresponding to a subset of cells of the lattice, so as to form the pattern, wherein the cells of the bi-dimensional lattice comprise islets protruding from the surface of the device and each cell of the subset of cells comprises one of the spots of material formed on top of one of the islets.

2. The test device according to claim 1, wherein the flow path comprises reagents for enabling said diagnostic testing; and
    the spots are located downstream the reagents with respect to the liquid inlet.

3. The test device according to claim 1, wherein the flow path is a first flow path and said device comprises a second flow path extending from said liquid inlet.

4. The test device according to claim 2, wherein the surface is a surface of a material impregnated with the reagents.

5. The test device according to claim 2, wherein the device comprises one or more microchannels, wherein one of the one or more microchannels comprises the spots of material.

6. The test device according to claim 1, wherein the device further comprises a cover covering the pattern of spots, where the cover is transmissive to light.

7. The test device according to claim 1, wherein the spots are inkjet spotted spots of material.

8. The test device according to claim 1, wherein the spots comprise, each, one or more of: dyes, pigments, liquid metals, liquid alloys, colloids, and proteins.

9. The test device according to claim 1, wherein at least some of the spots comprise, each, a temperature-sensitive indicator.

10. A test device configured for diagnostic testing, the device comprising:
    a liquid inlet;
    a flow path extending from said liquid inlet;
    an optical readable medium, the medium comprising a pattern of spots of material arranged on a surface of the device, within the flow path, wherein the spots are arranged according to a bi-dimensional lattice and are located at positions corresponding to a subset of cells of the lattice, so as to form the pattern, wherein each cell of the subset of cells comprises one of the spots of material formed on top of an islet protruding from the surface of the device,
    wherein the spots are of a first material and the device further comprises additional spots of a second material, wherein the spots and the additional spots are identical in appearance before exposure to a liquid to be used for the diagnostic testing, the first material and the second material have a substantially different solubility in the liquid to be used for the diagnostic testing, and the additional spots are located at positions corresponding to other cells of the lattice, distinct from the subset of cells,
    wherein after the diagnostic testing the optical readable medium displays the pattern of spots and before the diagnostic testing the optical readable medium displays a different pattern of the spots and the additional spots.

11. The test device according to claim 1, wherein a pitch between contiguous cells of the lattice is larger than or equal to 110 µm.

12. The test device according to claim 1, wherein the lattice comprises n×m cells, with each of n and m larger than or equal to 4.

13. The test device according to claim 1, wherein two contiguous islets are separated by a gap, which, on average, is larger than 10 µm.

14. The test device according to claim 1, wherein an average height of the islets is larger than or equal to 5 µm, wherein the average height is measured perpendicularly to an average plane of the surface.

15. The test device according to claim 1, wherein an average in-plane dimension of the islets is larger than or equal to 100 µm, wherein the average in-plane dimension is measured parallel to an average plane of the surface.

16. The test device according to claim 1, wherein the device comprises a surface material that is one of the following materials: a polymer, silicon dioxide, glass, and cellulose, and
    the surface on which the flow path is formed is formed of the surface material.

* * * * *